(12) United States Patent
Nicholls et al.

(10) Patent No.: US 8,841,633 B2
(45) Date of Patent: Sep. 23, 2014

(54) METHOD AND APPARATUS FOR DETECTING PHARMACEUTICALS IN A SAMPLE

(76) Inventors: Ian A Nicholls, Kalmar (SE); Bjorn C.G. Karlsson, Kalmar (SE); Annika M Rosengren, Kalmar (SE); Per Ola Andersson, Umea (SE)

( * ) Notice: Subject to any disclaimer, the term of this patent is extended or adjusted under 35 U.S.C. 154(b) by 455 days.

(21) Appl. No.: 13/263,399

(22) PCT Filed: Mar. 25, 2010

(86) PCT No.: PCT/SE2010/050326
§ 371 (c)(1),
(2), (4) Date: Oct. 7, 2011

(87) PCT Pub. No.: WO2010/117320
PCT Pub. Date: Oct. 14, 2010

(65) Prior Publication Data
US 2012/0032095 A1    Feb. 9, 2012

(30) Foreign Application Priority Data
Apr. 7, 2009  (SE) ...................................... 0950225

(51) Int. Cl.
G01J 1/58    (2006.01)
G01N 21/64   (2006.01)

(52) U.S. Cl.
CPC ................................. G01N 21/6408 (2013.01)
USPC .................................... 250/458.1; 250/459.1

(58) Field of Classification Search
USPC .......................................... 250/458.1, 459.1
See application file for complete search history.

(56) References Cited

U.S. PATENT DOCUMENTS 6,673,622 B1 * 1/2004 Jina .................................. 436/69
7,154,102 B2 * 12/2006 Poteet et al. ................... 250/372

FOREIGN PATENT DOCUMENTS

| JP | 2007-033159 A | 2/2007 |
| JP | 2007-504462 A | 3/2007 |
| WO | 2004/090517 A1 | 10/2004 |
| WO | 2005/036175 A | 4/2005 |

OTHER PUBLICATIONS

International Search Report; mailed Jul. 16, 2010; PCT/SE2010/050326.
Björn C.G. Karlsson; "The Spectrophysics of Warfarin: Implications for Protein Binding", Journal of Physical Chemistry B. American Chemical Society USA, vol. 111, No. 35, Spe. 6, 2007, pp. 10520-10528, XP002588904, ISSN: 1089-5647, pp. 10522, col. 1, line 6; p. 10524, col. 2, last line; p. 10526, col. 1, line 9; p. 10527, col. 1, line 22; p. 10527, col. 2, lines 21-27, figures 1,4.

(Continued)

Primary Examiner — David Porta
Assistant Examiner — Mindy Vu
(74) Attorney, Agent, or Firm — Ladas & Parry LLP

(57) ABSTRACT

A method and apparatus for measuring a vitamin K antagonizing anticoagulant present in a sample (116), arranged to: irradiate (304) the sample (116) with light from a light source (114) for exciting the anticoagulant through its absorption of the light, the excitation of the sample (116) resulting in a fluorescent emission from the sample (116); measure (306) the fluorescent emission from the sample (116); determine (308) a fluorescence lifetime ($T_1$) of the fluorescent emission of the sample (116); determine (310) an intensity ($A_1$) of the fluorescent emission at the fluorescence lifetime ($T_1$); and determine (312) a amount (c) of the anticoagulant, as a function of the intensity ($A_1$) of the fluorescent emission at the fluorescence lifetime ($T_1$).

22 Claims, 3 Drawing Sheets

(56) References Cited

OTHER PUBLICATIONS

Charles E. Petersen, et al; "Probing the Structure of th Warfarin-Binding Site on Human Serum Albumin Using Site-Directed Mutagenesis", Proteins, vol. 47, No. 2, May 1, 2002, pp. 116-125, XP002588905 ISSN: 0887-3585, p. 117, col. 2, line 4, p. 118, col. 1, line 30.

Chung-Eun Ha, et al; "Investigations of the Effects of Ethanol on Warfarin Binding to Human Serum Albumin", Journal of Biomedical Science, vol. 7, No. 2, Mar. 2000, pp. 114-121, XP002588906; ISSN: 1021-7770.

Svante Lifvergren, et al; Online Statistical Monitoring of Critical Patient Data increases Patient Safety, PICMET 2008 Proceedings, Jul. 2008, pp. 895-899, XP002588907 paragraph [001.]

Avraham Yacobi, Ph.D, et al; "Serum protein binding as a determinant of warfarin body clearance and anticoagulant effect", Clin. Pharmcol. Ther., 1976, 19, pp. 552-558; Received for publication Sep. 29, 1975, Accepted for publication Jan. 9, 1976.

J. Sérgio Seixas De Melo, et al; "Photophysical Behavior of Coumarins as a Function of Substitution and Solvent: Experimental Evidence for the Existence of a Lowest Lying $^1(\eta,\pi^*)$ State", The Journal of Physical Chemistry, vol. 98, No. 24, pp. 6054-6058, Jun. 1994.

\* cited by examiner

METHOD AND APPARATUS FOR DETECTING PHARMACEUTICALS IN A SAMPLE

TECHNICAL FIELD

The invention relates to a method and apparatus for measuring a vitamin K antagonizing anticoagulant present in a sample.

BACKGROUND ART

Today, many pharmacologically active drugs can be effective in vivo only if they are able to achieve and maintain therapeutic concentrations at the site of action. Pharmaceutical properties such as solubility, partition coefficient, permeability, and protein binding contribute to in vivo disposition and, frequently, these properties are important determinants of clinical outcome. The recent successes of combinatorial chemistry in accelerating drug discovery have also increased the interest in rapid, resource-sparing approaches to determining pharmaceutical properties.

The binding of drugs to serum proteins is particularly important, because it affects both the activity of drugs and their disposition. According to the "free drug" hypothesis, only unbound drug exerts pharmacological activity and disposition is often altered by drug binding. Consequently, it is important to know the affinity of a drug for serum proteins.

An example of such a drug is warfarin which is a vitamin K antagonizing anticoagulant derived from coumarin. Warfarin is a clinically important drug widely used in the treatment of thrombolic disorders such as heart attacks and stroke. The mechanism of action of this drug is based on an inhibition of the enzyme vitamin-K dependent reductase (VKOR) which is important for the coagulation of blood. When introduced into blood plasma, 99% of warfarin is reported to be bound to the blood plasma transport protein, human serum albumin (HSA) (Yacobi et al., Clin. Pharmcol. Ther. 1976, 19, 552-558). On account of the fact that HSA demonstrates polymorphism, and that the therapeutic window of the drug is very narrow, careful monitoring of the effect of drug dosage must be performed.

Moreover, other factors have been shown to impact upon the anticoagulant effect of warfarin, e.g. food intake and metabolic rates. Currently, the inhibition of VKOR by warfarin is measured by an indirect method in which the clotting time (prothrombin time) is measured. As self-monitoring with this method is problematic, the development of alternative methods, ideally both more robust and more sensitive, for determination of an amount or concentration of e.g. warfarin present in a patients blood is desirable.

It should be noted that other techniques have been proposed for protein binding measurements including dialysis, ultrafiltration, circular dichroism, and extrinsic fluorescence.

SUMMARY

In view of the foregoing, it is an object of the invention to provide an improvement of the above techniques and prior art. More particularly, it is an object to provide a method and apparatus for efficiently detecting an amount of a vitamin K antagonizing anticoagulant such as warfarin present in a patient.

Hence a method is provided for measuring a vitamin K antagonizing anticoagulant present in a sample, the method comprising: irradiating the sample with light from a light source for exciting the anticoagulant through its absorption of the light, the excitation of the sample resulting in a fluorescent emission from the sample; measuring the fluorescent emission from the sample; determining a fluorescence lifetime of the fluorescent emission of the sample; determining an intensity (amplitude) of the fluorescent emission at the fluorescence lifetime; and determining an amount of the anticoagulant, as a function of the intensity of the fluorescent emission at the fluorescence lifetime.

The fluorescence lifetime and the intensity described above may be referred to as a first fluorescence lifetime and a first intensity, in which case the method may comprise: determining i) a second or ii) a second and a third fluorescence lifetime of the fluorescent emission of the sample; determining intensities of the fluorescent emission at the respective fluorescence lifetime; and determining the amount of the anticoagulant, as a function of the intensities of the fluorescent emission at the respective fluorescence lifetimes.

Determining an amount of warfarin also comprises the possibility to determine a concentration of warfarin, as a concentration-value is associated with an amount-value. Accordingly, an "amount" can herein be read as a "concentration" and vice versa, as long as the concentration-value may be determined by using the amount-value in combination with a volume-value of the sample.

According to another aspect of the invention, an apparatus is provided for measuring a vitamin K antagonizing anticoagulant present in a sample, the apparatus comprising: a light source arranged to irradiate the sample with light for exciting the anticoagulant through its absorption of the light, the excitation of the sample resulting in a fluorescent emission from the sample; measuring means arranged to measure the fluorescent emission from the sample; and at least one processor configured to i) determine a fluorescence lifetime of the fluorescent emission of the sample, ii) determine an intensity of the fluorescent emission at the fluorescence lifetime, and iii) determine an amount of the anticoagulant, as a function of the intensity of the fluorescent emission at the fluorescence lifetime.

The inventive apparatus may comprise means for or be configured to execute any of the features described above and below in association with the inventive method, and has the corresponding advantages. In particular a second or a second and a third fluorescence lifetime with associated intensities may be determined and used for estimating the amount.

In brief, the fluorophoric nature of warfarin's coumarin ring structure (de Melo et al., J. Phys. Chem. 1994, 98, 6054-6058) will allow for the time-resolved fluorescence spectroscopic detection of this drug.

Recent research (Karlsson et al., J. Phys. Chem. B 2007, 111, 10520-10528) using a series of theoretical and spectroscopic studies that highlight the complex nature of warfarin, and in particular its medium dependent isomerization, which may illustrate why e.g. spectroscopy-based methods for the direct determination of warfarin have not been forthcoming.

The unraveling of the relationship between molecular environment, isomeric distribution and the spectroscopic characteristics of warfarin has unexpectedly provided the basis for developing warfarin-detection and -quantification methods, which can discriminate between warfarin in various states, e.g. bound to a protein or free in plasma.

As indicated, the invention provides a time-resolved fluorescence spectroscopic detection and quantification of warfarin bound to a protein or free in plasma. In further detail, this facilitates a novel alternative method for the efficient and direct monitoring of warfarin's effect on blood coagulation.

BRIEF DESCRIPTION OF THE DRAWINGS

Embodiments of the invention will now be described, by way of example, with reference to the accompanying schematic drawings, in which.

DETAILED DESCRIPTION OF PREFERRED EMBODIMENTS

Figure 1:
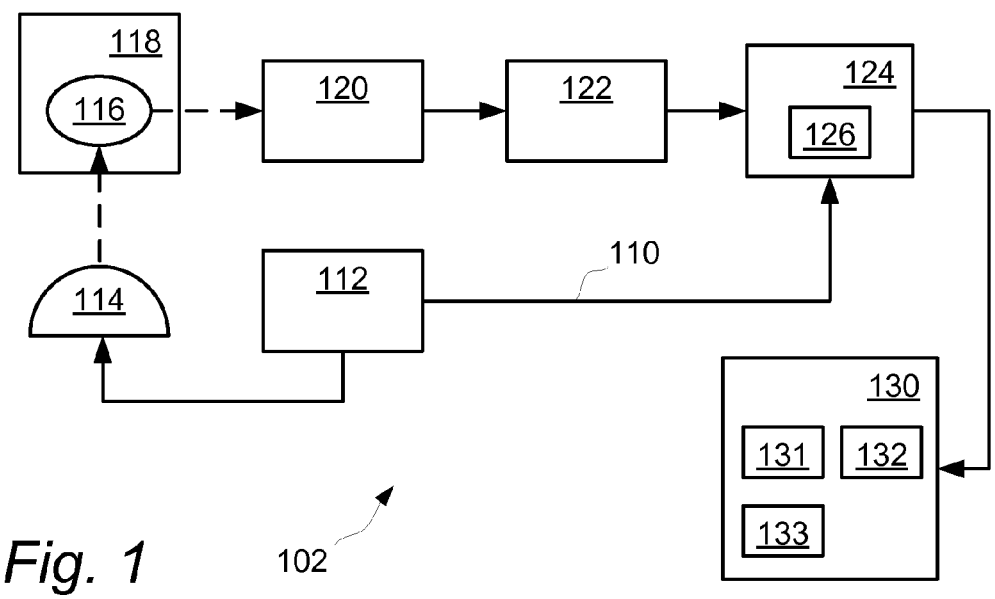
FIG. 1 illustrates an apparatus according to the invention for detecting a vitamin K antagonizing anticoagulant.

With reference to FIG. 1, an apparatus 102 for detecting a vitamin K antagonizing anticoagulant has a receptacle 118 which contains a sample 116 to be analyzed for the presence of a pharmaceutical such as warfarin or any other derivate of coumarin.

An excitation light source 114 for repeatedly irradiating the sample 116 with pulses of excitation light is provided. The light source 114 is preferably a pulsed laser but may also be a light emitting diode. A light source driving and controlling unit 112 comprises a laser power supply and is arranged to generate a triggering signal 110 to a photon timing unit 124. The repetition rate of the excitation light is sufficiently low to allow a substantial decay of the fluorescence of the sample 116 before the next exciting pulse. A pulsing frequency of for example around 1 MHz would commonly be appropriate. The duration of the pulse of excitation light should be significantly shorter than the fluorescence lifetime of the fluorophore (i.e. the pharmaceutical) in order to obtain reliable lifetime measurements.

A typical fluorophore has a fluorescence lifetime in the range of 0.02-20 ns and a suitable length of the light pulse would be in the order of 0.001 ns. The frequency of the pulse is an example of a parameter typically adjusted for the sample under investigation. In addition, the light source 114 and the light source driving and controlling unit 112 facilitates adjustment of other parameters such as the number of pulses and the intensity of the excitation light in order to account for e. g. the amount of fluorophore in the sample, the needed accuracy in the result etc. Light sources, e. g. pulsed lasers or light emitting diodes, with the characteristics described above and with driving and controlling units therefore are known in the art and commercially available.

Positioned adjacent to the receptacle 118 containing the sample 116 is a photodetector 120 which has the purpose of detecting the emitted fluorescent photons. Different optical components are placed between the sample 118 and the detector 120. For example several lenses are used to maximize the amount of fluorescent light collected from the sample 118 and to focus the light onto the detector 120. Furthermore dichroic mirrors and filters may be used to select a range of wavelength and prevent the excitation light from reaching the detector 120 and only let the light having a range of wavelength corresponding to the fluorescence spectrum of the fluorophore reach the detector 120.

An optical component may also be used to split the beam of the fluorescent light into several beams that are then directed to different detectors. This beam-splitting can be achieved in different ways, e. g. by using a beam splitter cube or by using multi-branch fiber optics. Such components are well known in the art and are commercially available on the market.

The photodetector 120 preferably comprises a photon counting photomultiplier tube (PMT) but other detectors such as an avalanche photodiode can be used. The signal from the photodetector 120 is typically amplified in a pre-amplifier 122. After amplification, the signal can go through a discriminator unit that remove any unwanted noise from the signal and only leave the electrical pulses generated by the photons on the PMT. The discriminator unit is then connected to a photon timing unit 124.

The photon timing unit 124 comprises a fast analogue-to-digital converter (A/D converter) and a memory for storing datapoints. As discussed above, it is possible for more than one photon per excitation, resulting from the excitation light pulse, to be recorded by the photodetector 120 and the photon timing unit 124. A photon detected by the PMT will give rise to an output pulse and to identify a PMT pulse position in time a suitable number (such as 6-10) data points per pulse are collected.

The collected data points are analyzed by an arrival time determination module 126, which is realized as a software program module residing either within the photon timing unit 124 or alternatively within an external computer 130, to determine the arrival time of the fluorescence photons. Examples of suitable algorithms for arrival time determination are known within the art and implemented in presently available equipments.

An analyzing module 132 is arranged to receive and analyze a dataset of photon arrival times from the arrival time determination module 126. This module 132 is preferably a software program module 131 implemented in and executed on the computer 130. The computer 130 is a microprocessor with an associated memory device (not shown) but may be a conventional PC. The microprocessor 130 is equipped with communication means (not shown) connected to other units of the system 102.

Installed in and executing on the microprocessor 130 is also a software program module for measurement control 133. As the skilled person realizes, the installation of and execution of the software modules 126, 132 and 133 per se can be done in various ways and in various computer configurations. For example the measurement control unit 133 can be executed in a PC suitable for laboratory conditions, the arrival time determination module 126 can be incorporated within the photon timing unit, and the analyzing module 132 in a special purpose machine can be designed for the high computational speed needed for certain analysis.

The photodetector 120, the pre-amplifier 122 and the photon timing unit 124 may in combination be seen as measuring means arranged to measure the fluorescent emission from the sample 116, while the computer 130 may be the processor that executes software instructions that implement the method described below.

Figure 2:
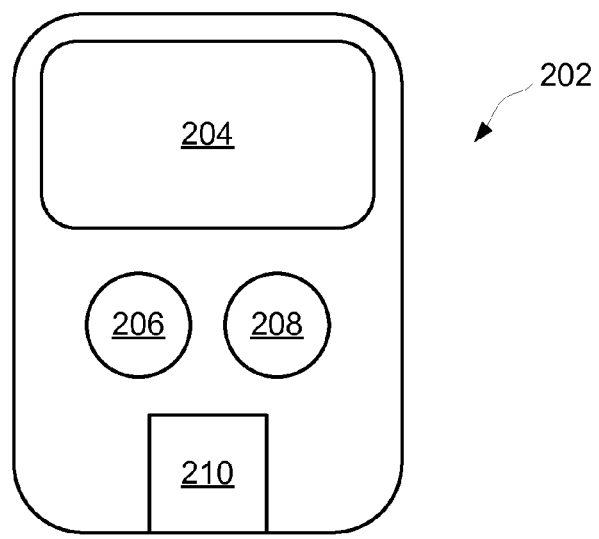
FIG. 2 illustrates a user equipment incorporating the apparatus of FIG. 1.

However, the apparatus 102 is preferably incorporated in a small portable unit 202 as illustrated in FIG. 2. This unit 202 has a LCD display 204 for user interaction and maneuvering buttons 206, 208 for operating the device via commands like "on/off", "perform measurement" etc. A receptacle 210 is arranged on the front side of the device 202 for receiving the sample, and the remaining components of the apparatus of FIG. 1 are arranged internal of the portable device 202. Preferably the device 202 is powered by an internal battery but an adaptor unit may be used as well.

As will be described below, quite specific values of fluorescence lifetimes and associated intensity values are to be determined in case warfarin is the pharmaceutical to be detected, which allows the components of the apparatus 102 to be optimized and thus made smaller when used in the device 202.

Figure 3:
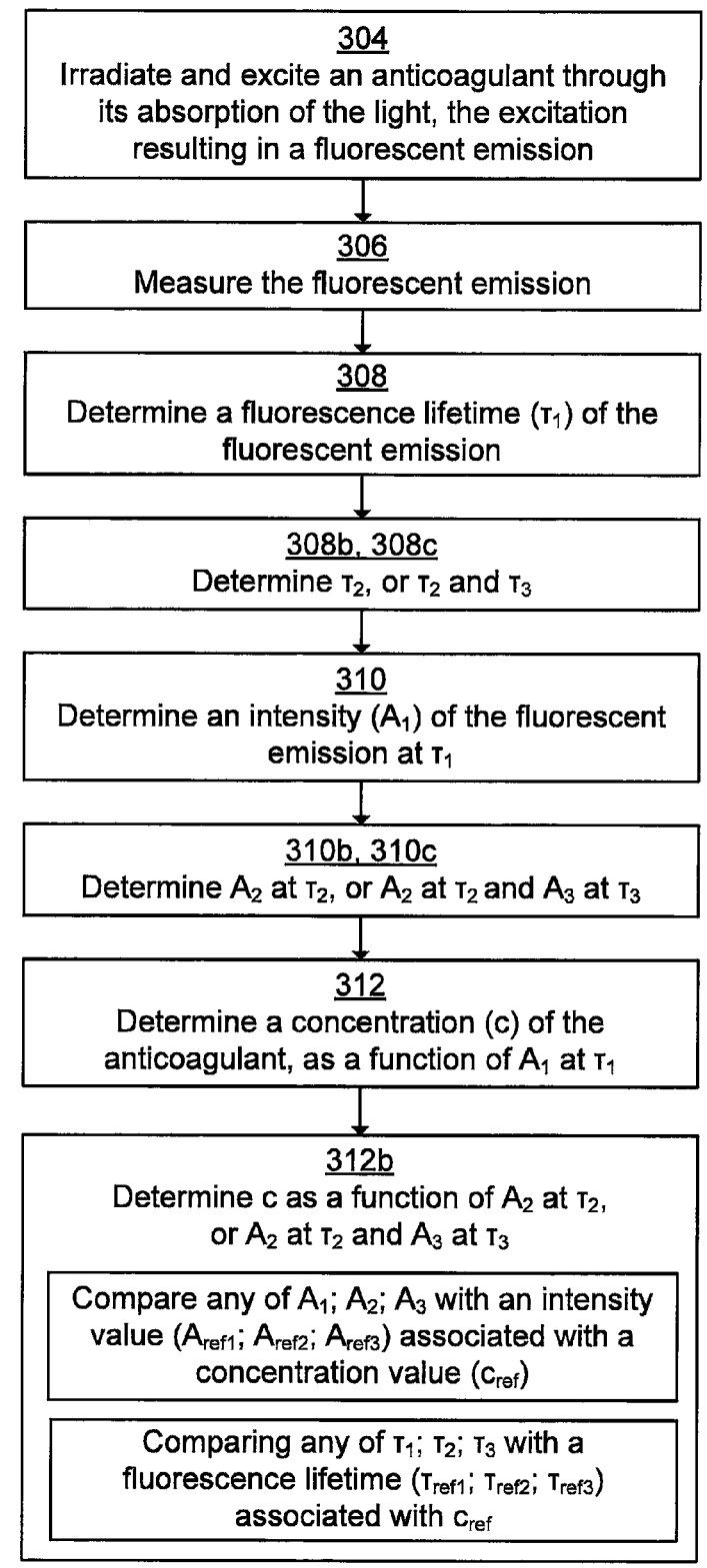
FIG. 3 shows a flowchart of the measurement and analyzing method according to an embodiment of the invention.

With reference to FIG. 3 the method performed in the apparatus is described, which performs steps for measuring a vitamin K antagonizing anticoagulant like warfarin present in the sample 116.

The method may be implemented as software instructions, i.e. a computer program code for carrying out methods disclosed herein may for development convenience be written in a high-level programming language such as Java, C, and/or C++ but also in other programming languages, such as, but not limited to, interpreted languages. Some modules or routines may be written in assembly language or even microcode to enhance performance and/or memory usage. It will be further appreciated that the functionality of any or all of the functional steps of the method may also be implemented using discrete hardware components, one or more application specific integrated circuits, or a programmed digital signal processor or microcontroller.

In the method, first the sample 116 is irradiated 304 with light from the light source 114 which excites the anticoagulant through the anticoagulants absorption of the light. The excitation of the sample 116 results in a fluorescent emission from the sample 116, and this fluorescent emission is measured 306. Next a fluorescence lifetime $\tau_1$ of the fluorescent emission is determined 308, and after this an intensity $A_1$ of the fluorescent emission at the fluorescence lifetime $\tau_1$ is determined 310. Finally an amount or concentration c of the anticoagulant is determined 312 as a function of the intensity $A_1$ at the fluorescence lifetime $\tau_1$.

A second fluorescence lifetime $\tau_2$ of the fluorescent emission of the sample 116 may be determined 308b, which can be is done simultaneously with the determining of the first fluorescence lifetime $\tau_1$. An intensity $A_2$ of the fluorescent emission at the second fluorescence lifetime $\tau_2$ is also determined 310b (at the same time and in the same manner as the determining of the first intensity $A_1$). In this case, when determining the amount c of the anticoagulant, the amount is determined 312b also as a function of the second intensity $A_2$ at the second fluorescence lifetime $\tau_2$ by using the values of $\tau_2$ and $A_2$ in a manner similar with using of $\tau_1$ and $A_1$. By taking the intensity at the second fluorescence lifetime into account it is possible to make a more "accurate" prediction of the amount of warfarin, since various states (e.g. unbound warfarin or warfarin bound to some protein) of warfarin appears to have different fluorescence lifetimes.

For the same purpose, a third fluorescence lifetime $\tau_3$ and a third intensity $A_3$ at the third fluorescence lifetime $\tau_3$ may be determined and used in a similar manner. This, in combination with the second lifetime $\tau_2$ and intensity $A_2$, is particularly relevant if warfarin's binding to HSA shall be taken into account when determining the best (unique) therapeutic window for different individuals.

The relevance of several lifetimes and intensities has been shown during tests by means of time-resolved fluorescence spectroscopic measurements in which the binding of warfarin to HSA in PBS (phosphate-buffered saline) buffer was investigated.

During these tests it was observed that excitation at 334 nm yielded information on the interaction of a deprotonated form of warfarin and HSA with three clearly distinguishable fluorescence lifetimes with $\tau_1$<100 ps, $\tau_2$≈1–1.5 ns and $\tau_3$≈3–4 ns. On excitation at 334 nm, while HSA is not excited, the deprotonated forms of warfarin contribute to the observed emission. Isolated warfarin in PBS yielded an unresolved excited state lifetime, i.e. $\tau_1$≤100 ps. From these experiments, the shortest fluorescence lifetime measured ($\tau_1$) was found to originate from the free unbound portion of warfarin in the solution, accessible to the bulk solvent, whereas, the two longer lifetimes ($\tau_2$, $\tau_3$) were found to originate from bound states to HSA. Accordingly, it has been shown that using several lifetimes will improve the accuracy in determining a proper warfarin dosage for each patient.

The determination of the amount c may comprise comparing the intensity $A_1$, $A_2$, $A_3$ of the at least one fluorescence lifetime $\tau_1$, $\tau_2$, $\tau_3$ with a known intensity value $A_{ref1}$, $A_{ref2}$, $A_{ref3}$ associated with a certain (known) amount value $c_{ref}$. In a similar manner the determination of c may comprise comparing at least one fluorescence lifetime $\tau_1$, $\tau_2$, $\tau_3$ with a known fluorescence lifetime $\tau_{ref1}$, $\tau_{ref2}$, $\tau_{ref3}$ associated with a certain amount value $c_{ref}$.

Figure 4:
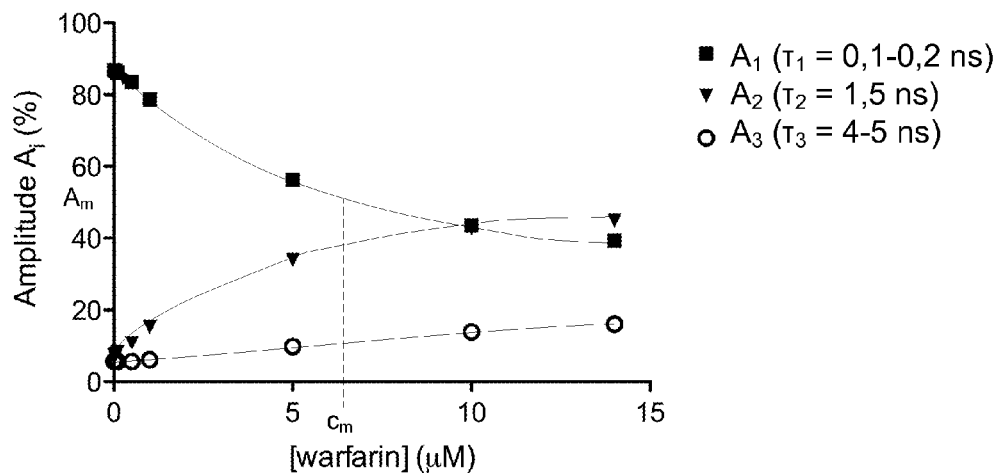
FIG. 4 illustrates an amount of warfarin at different fluorescence lifetimes and intensity values.

This comparison operation is further illustrated by the diagram of FIG. 4 where the x-axis represents the total amount of warfarin (which is related to the amount of warfarin) present in a sample of human blood (which substantially corresponds the amount present in a PBS buffer), and the y-axis represents the measured intensity values ($A_{ref1}$, $A_{ref2}$, $A_{ref3}$) as a percentage of the total amount a warfarin ($c_{ref}$), i. e the sum of $A_{ref1}$, $A_{ref2}$ and $A_{ref3}$ is 100% or 1.00. Since each intensity (amplitude) is associated with rather constant fluorescence lifetimes ($\tau_{ref1}$, $\tau_{ref2}$, $\tau_{ref3}$) it is possible to determine how much warfarin is bound to protein and how much that is not.

As indicated, the intensity values and fluorescence lifetimes of FIG. 4 corresponds the reference values $A_{ref1}$, $A_{ref2}$, $A_{ref3}$, and $\tau_{ref1}$, $\tau_{ref2}$, $\tau_{ref3}$, and by knowing $A_1$, $A_2$, $A_3$ and $\tau_1$, $\tau_2$, $\tau_3$ and by comparing these values with the reference values the amount of warfarin may be read from the diagram.

To improve the comparison the determination of the amount c may comprise using regression analysis for fitting at least one (but preferably all) intensity value $A_1$, $A_2$, $A_3$ of a fluorescence lifetime $\tau_1$, $\tau_2$, $\tau_3$ with a known intensity value $A_{ref1}$, $A_{ref2}$, $A_{ref3}$ associated with a certain amount value $c_{ref}$. The same applies for the fluorescence lifetime $\tau_1$, $\tau_2$, $\tau_3$, i.e. the determination of the amount c may comprise using regression analysis for fitting at least one fluorescence lifetime $\tau_1$, $\tau_2$, $\tau_3$ with a known fluorescence lifetime $\tau_{ref1}$, $\tau_{ref2}$, $\tau_{ref3}$ associated with a certain amount value $c_{ref}$. Applying regression analysis in this way is one example of using a correlation between the fluorescence lifetimes $\tau_1$, $\tau_2$, $\tau_3$ and known fluorescence lifetimes $\tau_{ref1}$, $\tau_{ref2}$, $\tau_{ref3}$ associated with a certain amount value $c_{ref}$, and other methods may be used as well.

The method may also comprise calculating a probability distribution when determining 310 an intensity value $A_1$, $A_2$, $A_3$ of the fluorescent emission at the fluorescence lifetime $\tau_1$, $\tau_2$, $\tau_3$. For this purpose as well as for performing the regression analysis mentioned above the publicly available GNU Scientific Library may be used.

As indicated, the measuring of the fluorescent emission from the sample comprises performing time-resolved fluorescence spectroscopic measurements. The light from the light source used has a substantially constant wavelength, and has more particularly a wavelength suitable for excitation of warfarin, such as a wavelength between 305 nm to 350 nm, or more specifically 334 nm. For improving the result the sample 116 may be stirred when performing the measuring of the fluorescent emission, which means that the receptacle comprises stirring-means.

To illustrate a numerical example using the diagram of FIG. 4, a blood sample from a patient may typically exhibit a first fluorescence lifetime $\tau_1$ with a measured intensity value $A_m$ of 0.51. In this case, as the dashed lines indicate in FIG. 4, the measured amount of warfarin $c_m$ is then 6.25 µM.

Accordingly, the measured intensity of the first fluorescence lifetime is compared with known intensity values (the values on the y-axis of FIG. 4) associated with a certain warfarin amount value (the values of the x-axis of FIG. 4). Since the proper curve (the one for the first fluorescence lifetime) is used, the determination of the amount also includes comparing the measured fluorescence lifetime with a known fluorescence lifetime (i.e. with one of the curves of the diagram in FIG. 4) associated with a certain warfarin amount-value.

Though the numerical example discusses the first fluorescence lifetime, the same applies for the second and third fluorescence lifetimes. Of courses, for improving the result various statistical methods may be used for weighting measured values of $A_1, A_2, A_3$ in order to improve the result, e.g. if they for reasons of varying measuring accuracy indicate slightly different amount values.

If a concentration should be determined from the amount of warfarin, the amount of warfarin is divided by the volume of the sample for which the amount was determined. Moreover, the distribution of $A_1, A_2, A_3$ may be used for analyzing the state of warfarin (unbound or a type of bound warfarin).

The amount of warfarin can also be used to determine a coagulation time of the blood. Coagulation time is however often individual for the patient from which the sample was taken, and for correlating the coagulation time with an amount/concentration value of warfarin empirical methods can be used, i.e. a set of coagulation times are determined for a set of blood samples having different amount/concentration values of warfarin. However, once this correlation is done knowing the warfarin amount/concentration value is sufficient for determining whether the drug is within its therapeutic window.

EXAMPLE

When generating the data (see FIG. 4) necessary for determining the amount in an arbitrary sample as described above, an experimental version of the apparatus of FIG. 1 was used for human blood buffered with a phosphate-buffered saline (PBS). It should be noted that even if a buffering solution was used, substantially the same results are obtained for blood obtained directly from a human. In any case, the experimental apparatus version may operate in the same manner as the apparatus 102 of FIG. 1.

In the experimental apparatus version time-resolved fluorescence spectroscopic measurements were performed on a time-correlated single-photon counting (TCSPC) system, IBH 5000M (Jobin Yvon IBH Ltd., Glasgow, UK). The fluorescence lifetimes (decay times) $\tau_i$ with associated amplitudes $A_i$ were determined using a light emitting diode, NanoLED-17 (HORIBA Jobin Yvon IBH) producing 334 nm (warfarin-human blood plasma binding experiments in PBS) and excitation pulses at 1.0 MHz repetition rates. A single grating monochromator (Model 5000M IBH) with a spectral bandwidth set to 32 nm was used. The data were collected in 4048 channels and the time-calibration was 13.4 ps/channel. The fluorescence emission was detected by an IBH TBX-04 photon detection module under TCSPC conditions, and the full width at half maximum (fwhm) of the instrumental response function was typically around 560 ps, which was measured with a suspension of silica particles (Ludox TMA-34 Sigma-Aldrich) dissolved in deionized water.

All experiments were performed monitoring the kinetics, mainly at 390 nm (warfarin-human blood plasma binding experiments in PBS) at an angle of 90° relative the excitation light. Time-resolved fluorescence data were analyzed using IBH DAS6 decay analysis software, which functions based upon least-squares fitting algorithms and reconvolution with the experimental response function. Three decay times were generally needed to obtain satisfying fitting results, i.e. $X^2 \leq 1.2$. The fitting results from the time (t) dependency were presented as amplitudes $(A_i)$ and decay times $(96_i)$ in relation to Equation (2):

$$F(t) = A_0 + A_1 e^{-\frac{t}{\tau_1}} + A_2 e^{-\frac{t}{\tau_2}} + A_3 e^{-\frac{t}{\tau_3}}$$

Freshly frozen plasma were obtained and initially human blood was collected in tubes with additives of citrate. In a second step, plasma was separated by centrifugation at 3000-3500×g at room temperature for 20 min and finally stored at −80° C. The buffer used was phosphate-buffered saline (PBS) consisting of 0.5 M $Na_2HPO_4$ (Scharlau)/$KH_2PO_4$ (Merck) and 0.1 M NaCl at pH 7.3.

All fluorescence spectroscopic measurements were typically performed under continuous stirring using a standard quartz-cuvette (1 cm path length, total volume 3 mL) at room temperature. Prior to the fluorescence experiments, studying the binding of warfarin to blood serum plasma proteins, samples of freshly frozen plasma were defrosted at 37° C. and aliquots (600 µL) were as may bee seen in table 1 below mixed with various amounts within the therapeutic window of the drug (0.1-14 µM) of warfarin in PBS (total volume 2 mL, incubation time 10 min).

Data obtained by the experiments are illustrated in table 1 below.

TABLE 1

| | [Warfarin] | Lifetimes (ns) | | | Amplitude (%) | | | |
|---|---|---|---|---|---|---|---|---|
| | µM | $\tau_1$ | $\tau_2$ | $\tau_3$ | $A_1$ | $A_2$ | $A_3$ | $\chi^2$ |
| PLASMA (14 mg/mL) | 0 | 0.07 | 1.9 | 8.4 | 87 | 7 | 6 | 1.04 |
| | 0.5 | 0.07 | 1.8 | 7.8 | 84 | 11 | 6 | 1.09 |
| | 10 | 0.15 | 1.5 | 4.3 | 44 | 43 | 14 | 1.18 |
| HSA (0.65 mg/mL) | 10 | 0.22 | 1.3 | 3.7 | 25 | 46 | 29 | 0.82 |

For verifying the method and apparatus described herein further experiments have been conducted on samples taken from patients prescribed with warfarin. In this verification, a series of experiments were conducted where amplitudes and lifetimes were measured for spiked samples of human blood (where the amount of warfarin was known). The results from these measurements were then used for determining the amount of warfarin in the blood of two patients prescribed with warfarin, based on the amplitudes at the respective fluorescence lifetimes.

In table 2 below the results from these further experiments are given, where fluorescence lifetimes $(\tau_i)$ in nanoseconds are given corresponding percentage values of relative amplitudes $(A_i)$ for different concentrations of warfarin in blood plasma (as in table 1 above). The values are given as mean values of three measurements±standard error of the mean.

TABLE 2

| [Warfarin] (μM) | Fluorescence lifetimes (ns) | | | Amplitudes (%) | | |
| --- | --- | --- | --- | --- | --- | --- |
| | $\tau_1$ | $\tau_2$ | $\tau_3$ | $A_1$ | $A_2$ | $A_3$ |
| 0.0 | 0.07 ± 0.01 | | 3.40 ± 0.07 | 97.2 ± 0.1 | | 2.8 ± 0.1 |
| 0.1 | 0.07 ± 0.01 | | 3.25 ± 0.04 | 96.8 ± 0.1 | | 3.2 ± 0.1 |
| 0.5 | 0.08 ± 0.00 | 1.54 ± 0.02 | 4.54 ± 0.16 | 94.2 ± 0.2 | 3.7 ± 0.0 | 2.1 ± 0.2 |
| 1.0 | 0.08 ± 0.00 | 1.48 ± 0.04 | 4.12 ± 0.01 | 91.5 ± 0.3 | 5.8 ± 0.2 | 2.8 ± 0.1 |
| 2.0 | 0.09 ± 0.01 | 1.43 ± 0.07 | 3.78 ± 0.09 | 85.5 ± 1.6 | 9.9 ± 0.9 | 4.6 ± 0.8 |
| 5.0 | 0.10 ± 0.00 | 1.25 ± 0.04 | 3.22 ± 0.03 | 75.5 ± 1.3 | 16.2 ± 0.7 | 8.4 ± 0.7 |
| 10 | 0.12 ± 0.00 | 1.27 ± 0.06 | 3.11 ± 0.04 | 59.7 ± 2.5 | 24.9 ± 1.0 | 15.4 ± 1.6 |
| 15 | 0.14 ± 0.00 | 1.19 ± 0.09 | 2.96 ± 0.10 | 52.6 ± 4.9 | 27.9 ± 2.0 | 19.5 ± 3.2 |
| patient no. 1 | 0.10 ± 0.00 | 1.50 ± 0.04 | 4.05 ± 0.01 | 69.4 ± 0.2 | 21.0 ± 0.2 | 9.6 ± 0.1 |
| patient no. 2 | 0.06 ± 0.00 | | 2.77 ± 0.02 | 96.0 ± 0.3 | | 4.0 ± 0.3 |

Blood samples were taken from two patients (patient no. 1 and patient no. 2) that are treated with warfarin. In connection with the retrieval of the blood sample, the patients respective International Normalized Ratio (INR) were measured, which is a well known type of measure indicative of the coagulation of the blood. The INR measurements showed that patient no. 1 has an INR value of 3.0, while patient no. 2 has an INR value of 1.9.

Figure 5:
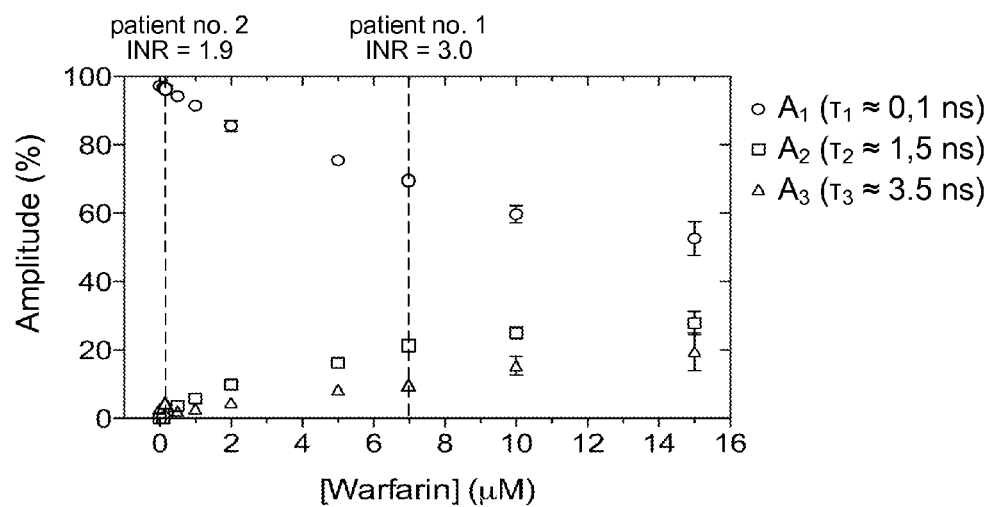
FIG. 5 illustrates the distribution of different fluorescence lifetimes at different amounts of warfarin and intensity values, as measured on spiked samples and samples taken from patients under warfarin therapy.

FIG. 5 graphically illustrates the numbers of table 2, where the results of the measurements for the patients (dashed vertical lines) can be found in relation to the measurements of the spiked samples. As can be seen from FIG. 5, the amplitude values for patient no. 1 corresponds to an amount of warfarin of 7 μM, while the amplitude values for patient no. 2 corresponds to approximately 0.2 μM. As can be seen, the experiments show a clear correlation between the INR, i.e. the coagulation of the blood, and the amount of warfarin in the blood.

Also, it is clear from the result that it is possible to measure the relative amount of bound/unbound warfarin while at the same time obtaining the total concentration, having in mind that the shortest fluorescence lifetime ($\tau_1$) typically originates from the unbound portion of warfarin while the two longer lifetimes ($\tau_2$, $\tau_3$) originate from bound states, as described above.

Although various embodiments of the invention have been described and shown, the invention is not restricted thereto, but may also be embodied in other ways within the scope of the subject-matter defined in the following claims. In particular, the invention may be implemented by using other techniques for exiting a sample. For example, the skin or the eye of a patient may be irradiated and the fluorescent emission from a pharmaceutical in the skin/eye is then measured. Subsequent steps are similar with the technique used when the sample is blood or any other body fluid, but as indicated, the "sample" must not necessarily be removed or taken from a patient.

The invention claimed is:

1. A method for measuring a vitamin K antagonizing anticoagulant present in a sample (116), the method comprising:
   irradiating (304) the sample (116) with light from a light source (114) for exciting the anticoagulant through its absorption of the light, the excitation of the sample (116) resulting in a fluorescent emission from the sample (116),
   measuring (306) the fluorescent emission from the sample (116),
   determining (308) a fluorescence lifetime ($\tau_1$) of the fluorescent emission of the sample (116),
   determining (310) an intensity ($A_1$) of the fluorescent emission at the fluorescence lifetime ($\tau_1$), and
   determining (312) an amount (c) of the anticoagulant, as a function of the intensity ($A_1$) of the fluorescent emission at the fluorescence lifetime ($\tau_1$).

2. A method according to claim 1, further comprising the steps of:
   determining (308b) a second fluorescence lifetime ($\tau_2$) of the fluorescent emission of the sample (116),
   determining (310b) an intensity ($A_2$) of the fluorescent emission at the second fluorescence lifetime ($\tau_2$), and
   determining (312b) the amount (c) of the anticoagulant, as a function of the intensity ($A_2$) of the fluorescent emission at the second fluorescence lifetime ($\tau_2$).

3. A method according to claim 2, further comprising the steps of:
   determining (308c) a third fluorescence lifetime ($\tau_3$) of the fluorescent emission of the sample (116),
   determining (310c) an intensity ($A_3$) of the fluorescent emission at the third fluorescence lifetime ($\tau_3$), and
   determining (312c) the amount (c) of the anticoagulant, as a function of the intensity ($A_3$) of the fluorescent emission at the third fluorescence lifetime ($\tau_3$).

4. A method according to any one of claims 1-3, wherein the determination (312) of the amount (c) comprises comparing the intensity ($A_1$; $A_2$; $A_3$) of at least one fluorescence lifetime ($\tau_1$; $\tau_2$; $\tau_3$) with a known intensity value ($A_{ref1}$; $A_{ref2}$; $A_{ref3}$) associated with a certain amount value ($c_{ref}$).

5. A method according to claim 1, wherein the determination (312) of the amount (c) comprises comparing at least one fluorescence lifetime ($\tau_1$; $\tau_2$; $\tau_3$) with a known fluorescence lifetime ($\tau_{ref1}$; $\tau_{ref2}$, $\tau_{ref3}$) associated with a certain amount value ($c_{ref}$).

6. A method according to claim 1, wherein the determination (312) of the amount (c) comprises using regression analysis for fitting at least one intensity value ($A_1$; $A_2$; $A_3$) of a fluorescence lifetime ($\tau_1$; $\tau_2$; $\tau_3$) with a known intensity value ($A_{ref1}$; $A_{ref2}$; $A_{ref3}$) associated with a certain amount value ($c_{ref}$).

7. A method according to claim 1, wherein the determination (312) of the amount (c) comprises using a correlation between at least one fluorescence lifetime ($\tau_1$; $\tau_2$; $\tau_3$) and at least one known fluorescence lifetime ($\tau_{ref1}$; $\tau_{ref2}$; $\tau_{ref3}$) associated with a certain amount value ($c_{ref}$).

8. A method according to claim 1, wherein the measuring (306) of the fluorescent emission from the sample (116) comprises performing time-resolved fluorescence spectroscopic measurements.

9. A method according to claim 1, wherein the vitamin K antagonizing anticoagulant is a synthetic derivative of coumarin.

10. A method according to claim 1, wherein the vitamin K antagonizing anticoagulant is warfarin.

11. A method according to claim 1, wherein the sample consists of human blood.

12. An apparatus for measuring a vitamin K antagonizing anticoagulant present in a sample (116), the apparatus comprising:
 a light source (114) arranged to irradiate (304) the sample (116) with light for exciting the anticoagulant through its absorption of the light, the excitation of the sample (116) resulting in a fluorescent emission from the sample (116),
 measuring means (120, 122, 124) arranged to measure the fluorescent emission from the sample (116), and
 at least one processor (130) configured to
  determine a fluorescence lifetime ($\tau_1$) of the fluorescent emission of the sample (116),
  determine an intensity ($A_1$) of the fluorescent emission at the fluorescence lifetime ($\tau_1$), and
  determine a amount (c) of the anticoagulant, as a function of the intensity ($A_1$) of the fluorescent emission at the fluorescence lifetime ($\tau_1$).

13. An apparatus according to claim 12, the one processor (130) further configured to:
 determine a second fluorescence lifetime ($\tau_2$) of the fluorescent emission of the sample (116),
 determine an intensity ($A_2$) of the fluorescent emission at the second fluorescence lifetime ($\tau_2$), and
 determine the amount (c) of the anticoagulant, as a function of the intensity ($A_2$) of the fluorescent emission at the second fluorescence lifetime ($\tau_2$).

14. An apparatus according to claim 13, the one processor (130) further configured to:
 determine a third fluorescence lifetime ($\tau_3$) of the fluorescent emission of the sample (116),
 determine an intensity ($A_3$) of the fluorescent emission at the third fluorescence lifetime ($\tau_3$), and
 determine the amount (c) of the anticoagulant, as a function of the intensity ($A_3$) of the fluorescent emission at the third fluorescence lifetime ($\tau_3$).

15. An apparatus according to any one of claims 12-14, the processor (130) further configured to determine the amount (c) by comparing the intensity ($A_1$; $A_2$; $A_3$) of at least one fluorescence lifetime ($\tau_1$; $\tau_2$; $\tau_3$) with a known intensity value ($A_{ref1}$; $A_{ref2}$; $A_{ref3}$) associated with a certain amount value ($c_{ref}$).

16. An apparatus according to claim 12, the processor (130) further configured to determine the amount (c) by comparing at least one fluorescence lifetime ($\tau_1$; $\tau_2$; $\tau_3$) with a known fluorescence lifetime ($\tau_{ref1}$; $\tau_{ref2}$; $\tau_{ref3}$) associated with a certain amount value ($c_{ref}$).

17. An apparatus according to claim 12, the processor (130) further configured to determine the amount (c) by using regression analysis for fitting at least one intensity value ($A_1$; $A_2$; $A_3$) of a fluorescence lifetime ($\tau_1$; $\tau_2$; $\tau_3$) with a known intensity value ($A_{ref1}$; $A_{ref2}$; $A_{ref3}$) associated with a certain amount value ($c_{ref}$).

18. An apparatus according to claim 12, the processor (130) further configured to determine the amount (c) by using a correlation between at least one fluorescence lifetime ($\tau_1$; $\tau_2$; $\tau_3$) and at least one known fluorescence lifetime ($\tau_{ref1}$; $\tau_{ref2}$; $\tau_{ref3}$) associated with a certain amount value ($c_{ref}$).

19. An apparatus according to claim 12, configured to measure the fluorescent emission from the sample (116) by performing time-resolved fluorescence spectroscopic measurements.

20. An apparatus according to claim 12, wherein the vitamin K antagonizing anticoagulant is a synthetic derivative of coumarin.

21. An apparatus according to claim 12, wherein the vitamin K antagonizing anticoagulant is warfarin.

22. An apparatus according to claim 12, wherein the sample consists of human blood.

* * * * *